United States Patent [19]

Chiang

[11] Patent Number: 4,936,828
[45] Date of Patent: Jun. 26, 1990

[54] LIQUID DROP IMAGE SENSOR

[76] Inventor: Kophu Chiang, 15 Colton Rd., Edison, N.J. 08817

[21] Appl. No.: 241,628

[22] Filed: Sep. 8, 1988

Related U.S. Application Data

[63] Continuation of Ser. No. 57,231, Jun. 2, 1987, abandoned.

[51] Int. Cl.$^5$ ............................................. A61M 5/16
[52] U.S. Cl. ..................................... 604/65; 604/253
[58] Field of Search ................................... 604/65–67, 604/251, 253; 128/DIG. 13; 73/861.41, 861.55

[56] References Cited

U.S. PATENT DOCUMENTS

| | | |
|---|---|---|
| 2,880,764 | 4/1959 | Pelavin . |
| 4,111,198 | 9/1978 | Marx et al. . |
| 4,173,224 | 11/1979 | Marx et al. . |
| 4,314,484 | 2/1982 | Bowman ........................ 73/861.41 |
| 4,432,761 | 2/1984 | Dawe ................................. 604/253 |
| 4,432,762 | 2/1984 | Dawe ................................. 604/253 |
| 4,490,801 | 12/1984 | Hagan et al. ....................... 364/564 |
| 4,820,281 | 4/1989 | Lawler, Jr. ......................... 604/253 |

Primary Examiner—Angela D. Sykes
Attorney, Agent, or Firm—Nydegger & Harshman

[57] ABSTRACT

A liquid drop images sensor for determining the volume of liquid drops comprises a light source and an array of optical sensors which receive light energy from the source. The array is positioned relative to the source to establish a passageway therebetween through which drops can fall. Electronic structure connected to the array sequentially activates the array for discrete episodes during the passage of a drop through the passageway. The electronic structure also generates signals which indicate the proportion of the array affected by the shadow of the drop during each episode. Additionally, the liquid drop image sensor includes structure which accumulates the signals and uses them to calculate the volume of the liquid drop.

19 Claims, 2 Drawing Sheets

LIQUID DROP IMAGE SENSOR

Background

This application is a continuation of application Ser. No. 057,231 filed on Jun. 2, 1987, now abandoned.

This invention relates generally to detectors which are used to determine the volume of fluid flow in a pipe or line. More particularly, the present invention relates to devices which determine volumetric flow rate by counting and/or analyzing a sequence of falling liquid drops that comprise the fluid flow. This invention is particularly, but not exclusively, suited for use with an IV administration system for the infusion of medical solutions to a patient.

Description of the Prior Art

Perhaps more so now than ever before, the need for precise, accurate and reliable determinations of volumetric fluid flow to a patient is recognized in the medical arts. Indeed, with certain of today's increasingly sophisticated medical procedures, the need for an accurate determination of the volume of fluids infused to a patient may be crucial.

At the outset, it must be recognized that in any IV administration system it is important to know whether there is, in fact, fluid flow. Typically, drip chambers have been employed in such systems for this purpose because they allow the attendant or operator to visually ascertain whether there is fluid flow in the line. The mere ability to observe fluid flow, however, is often not sufficient for the purposes of modern day technology. As is to be expected, various devices have been proposed which are intended to augment or complement the drip chamber and provide additional information required for the regulation of fluid flow to a patient. A simple roller clamp, when employed with an in-line drip chamber, is a very elementary means by which fluid flow to a patient can be grossly controlled. In its operation, the roller clamp is manipulated by a nurse or attendant to adjust the cross-sectional area of the IV tube for control of the fluid flow. Generally, the nurse or attendant manipulates the roller clamp until a desired rate of drops is observed in the drip chamber. Then, since an approximate value can be given for the volume of each drop passing into the drip chamber, the attendant can approximate the volumetric flow of fluid to a patient by merely counting the number of drops.

More sophisticated devices than the combination of a simple drip chamber and roller clamp have also been proposed for the purpose of determining the rate of fluid flow to a patient during IV infusion. Specifically, U.S. Pat. No. 3,985,133 which issued to Jenkins discloses a volumetric IV pump which is capable of infusing fluids to a patient at a predetermined rate. A device such as disclosed in the Jenkins patent is particularly well suited whenever a pumping mechanism is to be employed. Where pumps are not used, a device such as the one disclosed in U.S. Pat. No. 4,314,567 which issued to Cannon can be useful to control the rate of fluid flow.

Since the drip chambers are such a convenient component of an IV administration set, various devices have also been proposed which electronically observe fluid drops as they pass through the drip chamber. In each case the object is to determine the volume of fluid flow through the drip chamber. For example, U.S. Pat. No. 4,314,484 which issued to Bowman discloses a device that uses an optical detector in association with a drip chamber to count the number of drops that fall through the drip chamber. In addition to counting drops, Bowman converts the numerical accumulation of drops into a volumetric measurement by multiplying the number of drops by the average volume of fluid contained in each drop. Recognizing at least one factor that can affect this rather rough computation, the Bowman device compensates for the tendancy of the drop volume to change as a function of drop rate.

Still another example of a device which counts the drops falling through a particular space to determine fluid volumetric flow rate is disclosed in U.S. Pat. No. 2,880,764 which issued to Pelavin. Unlike Bowman, the Pelavin device determines the size of individual drops and calculates their fluid volume using the assumption that all drops are spherical in form. Thus, the Pelavin device is able to convert the number of drops into a volume of fluid by the simple calculation of an algorithm which considers that each drop is spherical. Again, however, this assumption overlooks several factors tht pertain to drops and drop formation.

An article by Ferenchak, Collins and Morgan, published in *In Surgery*, Nov. 1971 entitled "Drop Size and Rate in Parenteral Infusion" recognizes several factors which contribute to variations in drop size. According to the Ferenchak article, these factors are: the orifice diameter of the drop former, the rate of drop formation and the nature of the fluid. More specifically, Ferenchak points out that increasing drop rates result in the formation of larger drops and, further, that solutions of different specific gravities and surface tensions are expected to form drops of different size even though they may come from the same orifice.

In addition to physical attributes of the fluid and the infusion set which affect and vary the volume of a drop as it is formed, it has also been determined that during its fall, a drop is not spherical. In fact, the drop does not maintain its shape and, instead, undulates or oscillates in an observable manner. Observations have shown that as a drop begins to fall it is slightly ellipsoidal with a long vertical axis. Although there are secondary oscillations during the fall of the drop, the predominant effect is an oscillation about its shape in a state of equilibrium, i.e. a sphere. It happens that at any time during its fall, the drop will generally be ellipsoidal with rotational symmetry about its vertical axis, i.e. its direction of fall. As the drop falls it will have major and minor axes that vary sinusoidally with time according to the expressions:

$$a(t) = a(0) [1 + \epsilon \sin(wt + \phi)]$$

$$b(t) = a(0) [1 + \epsilon \sin(wt + \phi)]$$

where
  w = the angular frequency and
  $\phi$ = phase of the oscillation
so that the volume of the drop is a constant which is given by the expression:

$$V = (4/3) \ a(t) \ [b(t)]^2$$
$$= (4/3) \ [a(0)]^3.$$

In the above equations $\epsilon$ is a number that indicates the amount of deviation from sphericity and the ratio of a to b will be time dependent with a maximum value of $[1+\epsilon]^{3/2}$ and a minimum of $(1-\epsilon)^{3/2}$. Experimentally, this ratio is seen to be as high as 2:1.

In light of the above, it will be appreciated that where the determination of volumetric flow rate is to be ascertained by observing the actual number of drops falling through the drip chamber, several factors need to be considered. The present invention recognizes that the assumption a drop will be spherical can lead to erroneous calculations of volumetric flow. Instead, it is to be understood that, although a drop will change shape during its fall, it will remain substantially symmetrical about its vertical axis. In light of this understanding the present invention recognizes that the area of the silhouette of the drop taken in a direction perpendicular to the vertical axis, i.e. direction of fall, of the drop can be used to calculate a very precise determination of the volume of the drop.

In accordance with the above, it is an object of the present invention to provide a device that is able to determine the rate of flow of fluid through an IV administration set by observing individual drops as they fall through a drip chamber that is incorporated into the IV administration set. It is another object of the present invention to provide a drop image sensor having means to make a significantly accurate determination of fluid volume in individual drops. It is yet another object of the present invention to provide a drop image sensor which is reliable, easy to use and relatively inexpensive.

SUMMARY OF THE INVENTION

A preferred embodiment of the novel drop image sensor comprises in combination a light emitter associated with an aperture and a collimating lens which provides a source of collimated light. The liquid drop image sensor also comprises an area array of light sensors which is spaced at a predetermined distance from the collimated light source to establish a gap or passageway therebetween. The drop image sensor of the present invention also includes means to activate the light source when a liquid drop falls through the gap or passageway to project a shadow image or silhouette of the drop on the array of light sensors. Electronic means associated with the array of light sensors senses the proportion of light sensors or pixels which have been sensitized or activated by light from the collimated light source and differentiates them from the light sensors which have not been activated by virtue of their being within the shadow of the liquid drop which is cast on the array of light sensors. Means are also included in the present invention to use the signal information from the array of light sensors for calculation of an algorithm that determines the volume of the liquid drop which has fallen through the passageway.

In an alternate embodiment of the present invention the light sensors or pixels are arranged as a line and discretely activated in sequential episodes as drops fall through the gap. In this alternate embodiment, as in the preferred embodiment, a series of signals are generated which depict the proportion of sensors activated by collimated light relative to those which are not activated by virtue of their being within the shadow of the liquid drop cast upon the array. In the alternate embodiment, each signal represents a slice width of the drop and an accumulation of this information provides a profile of the liquid drop which is usable by the calculating means to determine the volume of the liquid drop that has fallen through the passageway between the light source and the array.

The novel features of this invention, as well as the invention itself, both as to its organization and operation will be best understood from the accompanying drawings taken in conjunction with the accompanying description in which similar reference characters refer to similar parts and in which:

DESCRIPTION OF THE PREFERRED EMBODIMENT

Figure 1:
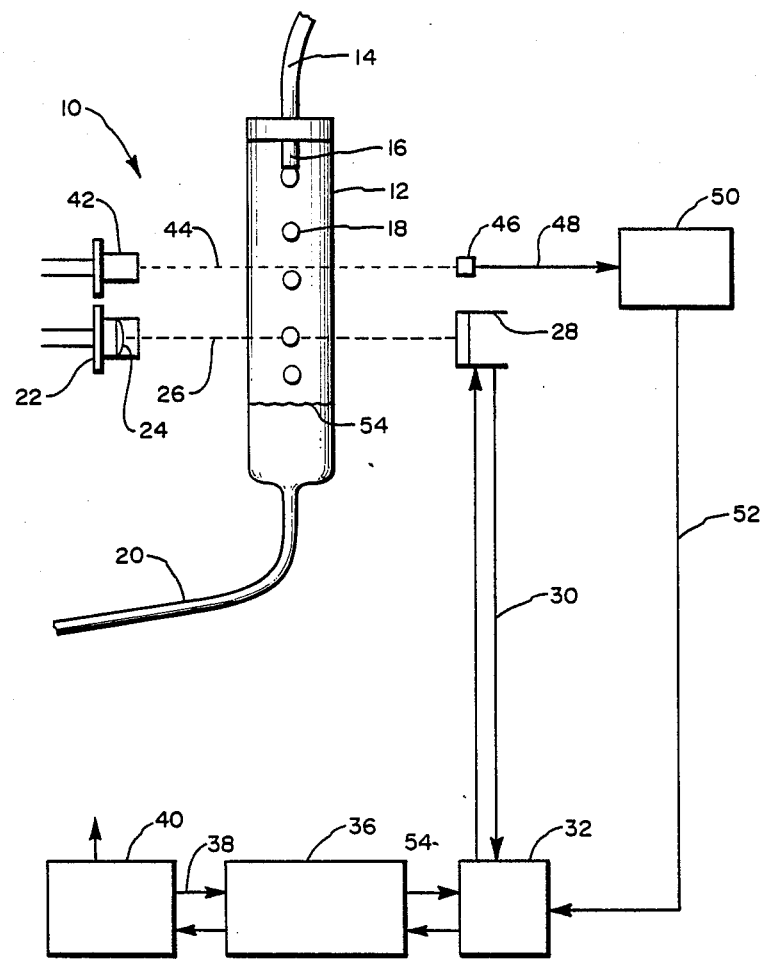
FIG. 1 is a schematic representation of the drop image sensor system showing the operational relationship of selected components.

Referring to FIG. 1, the liquid drop image sensor of the present invention is shown and is generally designated 10. As seen in FIG. 1, liquid drop image sensor 10 is associated with a drip chamber 12. As is well known by the person of ordinary skill, drip chamber 12 can be of any type generally available and typically used in IV administration sets for the infusion of fluids to a patient. In its operation drip chamber 12 is connected with an IV line 14 which transfers fluid or medical solutions from a fluid source (not shown) to the drip chamber 12. As fluid enters drip chamber 12, it passes through a drop former 16 where it is formed into drops of fluid 18. As seen in FIG. 1, drops 18, after separating from drop former 16, fall substantially along the longitudinal axis of drip chamber 12 and collect in the bottom of drip chamber 12. Upon leaving chamber 12 and the IV fluid passes through IV line 20 to the patient (not shown). It will be understood by the skilled artesan that for use with the liquid drop image sensor 10 of the present invention, drip chamber 12 must be made of a material through which light can pass. Preferably, chamber 12 is transparent.

A light emitting diode (LED) 22 is positioned with respect to the drip chamber 12 in a manner as substantially shown in FIG. 1. Although any wavelength of light can be used, LED 22 preferably emits infra-red light having a wavelength of approximately 900 mm. LED 22 may include a collimating lens 24 which, as is well known by the skilled artesan, is able to take light from a divergent source and cause the light to shine along parallel paths 26. Preferably collimating lens 24 is a plano-convex lens of focal length fairly near 63 mm. In accordance with the present invention, light emitted from LED 22 passes along the paths 26 through drip chamber 12 above the fluid level 54 and is incident on an array 28 of light sensors or pixels (not shown). For purposes of the present invention, array 28 may comprise a 1024 (CCD) element charged coupled device such as the array identified and sold as Fairchild CCD 133. Also it will be understood that the various components thus far discussed need to be arranged so that as drops 18 pass through chamber 12 they fall through light path 26 and interrupt part, but not all of the light path 26.

The optics for LED 22 and array 28 system are arranged so that infrared light from LED 22 is collimated by lens 24 and aimed at array 28. It will be understood by the skilled artesan that as a liquid drop 18 falls past array 28 the drop will block some of the light from LED 22 that is incident on array 28. Thus, a shadow of drop 18 is cast on the array 28 of photosensitive CCD elements (not shown). In one embodiment of the present invention, array 28 comprises an area of pixels (not shown) and the entire shadow of drop 18 is cast upon array 28. In an alternate embodiment, array 28 is substantially a line of pixels (not shown). With this linear arrangement, a series of one dimensional discrete cross-section slices of liquid drop 18, representing its width at various locations, are sequentially measured. In either embodiment, assuming that drop 18 has rotational symmetry about its vertical axis, a relatively simple algorithm for calculating the volume of drop 18 can be used.

Still referring to FIG. 1, it is seen that array 28 is electrically connected with a video decoder 32 by electrical connectors 30. Electrical connectors 34 connect video decoder 32 to a processor 36 which is connected to LED pulser 40 by electrical connectors 38. As will become subsequently more apparent, pulser 40 can be connected with LED 22 to cause intermittent and sequential illumination of the LED 22. On the other hand, LED 22 can provide a generally continuous light beam while the array 28 electronically provides for a sequencing of signals that are suitable for imaging the drops 18 in accordance with the present invention.

FIG. 1 also shows the electronic circuitry which provides for the triggering of either LED 22 or array 28. Specifically, a trigger light emitting diode (LED) 42 is provided to emit light along a path 44. As shown in FIG. 1, path 44 is located above light path 26 and is aimed to be incident upon a trigger photodiode 46. For purposes of the present invention, light path 44 must be positioned to pass through chamber 12 and be interrupted by drops 18 as they fall through chamber 12. As will be understood by the skilled artesan, interruption of light on path 44 by falling drop 18 will generate a signal at trigger photodiode 46 which can be transmitted through connector 48 to a preamplifier/trigger 50. The signal from preamplifier/trigger 50 can then be passed through connector 52 into the video decoder 32. At this point, the signal is processed by video decoder 32 to provide activation of LED 24 or array 28 in accordance with the desires of the operator for the purposes of imaging drops 18 in a manner as previously discussed.

Figure 2:
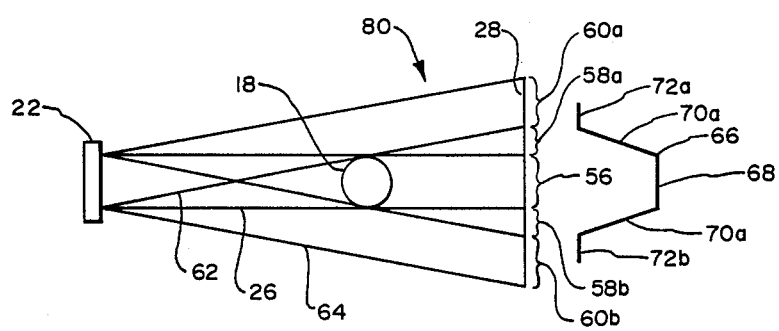
FIG. 2 is a schematic representation of light ray propagation from a divergent beam past a liquid drop.
Figure 3:
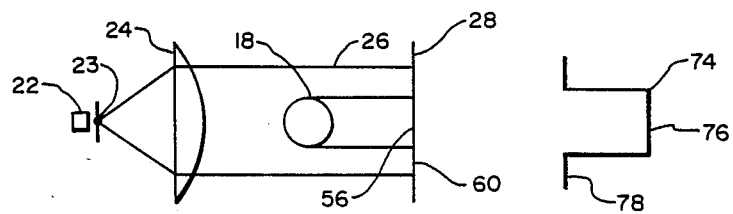
FIG. 3 is a schematic representation of collimated light propagation past a liquid drop.

Referring now to FIG. 2 and 3, the physical differences in the shadowing of drop 18 against array 28 using different light sources can be seen. For example, in FIG. 2 LED 22 produces divergent rays such as rays 62 and 64. It will be understood that light leaving LED 22 can take any path within the cone defined by divergent rays 62 and 64. On the other hand, with the incorporation of a collimating lens 24 as shown in FIG. 3, all divergent rays from LED 22 are collimated and it is seen that they follow generally parallel paths 26 as they pass through the gap 80 established between LED 22 and array 28. The collimation of light onto path 26 is facilitated by an aperture 23 place between LED 22 and lens 24. The presence of aperture 23 is important because it reduces the divergence of the beam collimated by the plano convex lens 24. This is because commercially available LEDs often have relatively large emitting areas, and the absence of a suitably sized aperture 23 may give rise to an unacceptably large divergent beam.

For purposes of understanding the signal which is generated by the liquid drop image sensor 10 of the present invention, reference is still made to FIG. 2 wherein a drop 18 is shown in the gap 80 between LED 22 and array 28. Recall that in FIG. 2 LED 22 is shown having a divergent light beam. As previously discussed, this results in divergent rays 62 and 64 emitting from LED. 22. The result, when the shadow of drop 18 is cast on array 28, is the creation of distinct regions thereon which can generally be defined in accordance with the amount of incident light. Specifically, in FIG. 2, a shadow area 56 is shown which represents the umbra or silhouette of drop 18 on array 28. This is the primary area of interest for sensor 10. However, because of the divergent nature of the light emitting from LED 22, other regions of array 28 are also affected by partial shadows. These partial shadows are shown as prenumbras 58a and b. It will be appreciated that penumbras 58a and b produce unwanted signals insofar as the depiction of the shadow 56 of drop 18 on array 28 is concerned. Further, FIG. 2 shows areas 60a and b which are not affected by the drop 18 and represent areas where direct light from LED 22 is incident upon array 28.

A signal 66, which also is shown in FIG. 2, corresponds generally to the intensity of light incident upon array 28. Specifically, low intensity region 68 of signal 66 corresponds to umbra or shadow 56 of drop 18 while the regions 70a and b respectively correspond to penumbras 58a and b and represent a varying intermediate intensity of light incident upon array 28. Further, the high intensity region 72a and b correspond to areas 60a and b where direct light is incident upon array 58. It will be appreciated by the skilled artesan that a signal, such as signal 66, can be somewhat troublesome for purposes of determining the actual outline of drop 18. Therefore, in accordance with the present invention, light emitting from LED 22 is collimated by aperture 23 and lens 24 in a manner that causes light passing through the lens 24 to align along generally parallel paths 26 as shown in FIG. 3.

In FIG. 3, a similar analysis of the incident light upon array 28 shows that with collimated light penumbras 58a and b have been essentially eliminated. This causes a shadow, umbra or silhouette 56 that corresponds very substantially with the actual outline of drop 18. Thus, areas 60 on array 28 are areas of direct light intensity. The result is the generation of a signal 74 having regions of low intensity 56 and high intensity 78 which establish a signal that will be recognized as being very useful for analysis with electronic componentry.

Figure 4A:
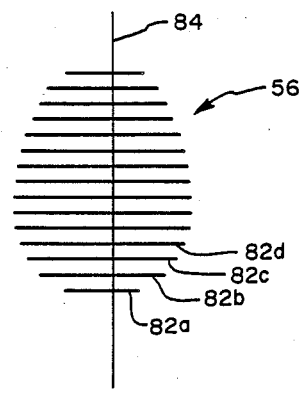
FIGS. 4A, B and C are representative electronic silhouettes of various water drops generated by the image sensor of the present invention.
Figure 4B:
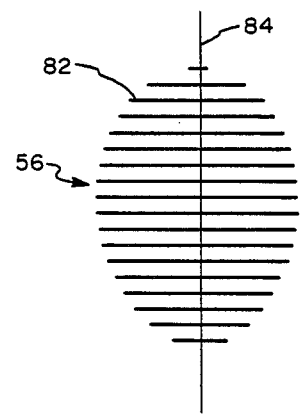
FIG. 4D is a representative electronic silhouette of a ball bearing generated by the image sensor of the present invention.
Figure 4C:
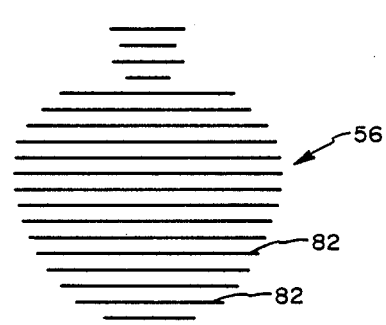
Figure 4D:
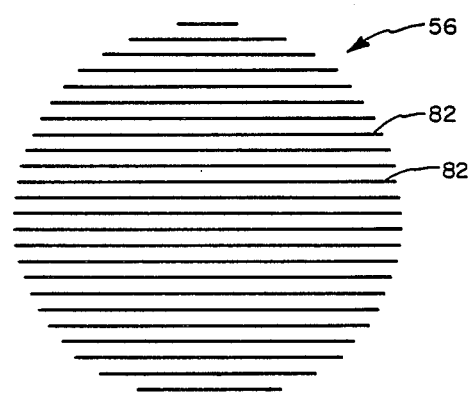

As stated above, array 28 may be linear in structure. In this case a complete silhouette of drop 18 cannot be detected. A linear array, however, can generate signals corresponding to slicer or width measurements of the drop 18. Typical signals generated by a linear array 28 in response to a drop 18 falling thorough light path 26, are similar to the representations presented in FIGS. 4a, b and c. With reference to FIG. 4a, it can be seen that the shadow or silhouette 56 of liquid drop 18 can be analyzed as a series of slices 82. Each individual slice 82 represents a signal generated during a discrete episodic activation of the array 28. For example, during one such episode, the slice 82a is generated. In subsequent episodes, slices 82b, c and d are sequentially generated. This continues until the entire drop 18 affects array 28. As previously mentioned and to be subsequently discussed in greter detail, the present invention includes means for accumulating the signals representing slices 82a, b, c, d, et seq. and using this information for calculating the volume of the drop. Appreciate that the calculation of drop volume is based on an assumption that the drop is symmetrical with respect to the vertical axis of the drop. For the shadow 56 of a drop 18 as shown in FIG. 4a, the vertical axis and axis symmetry is represented by the line 84. For purposes of comparison and illustration, representative silhouettes for a drop 18 at unspecified times during its fall through chamber 12 might be as shown in FIGS. 4b and 4c. For purposes of comparison only, FIG. 4d depicts signals generated for the shadow 56 of a ball bearing which was experimentally used in accordance with the practice of the present invention.

Figure 5:
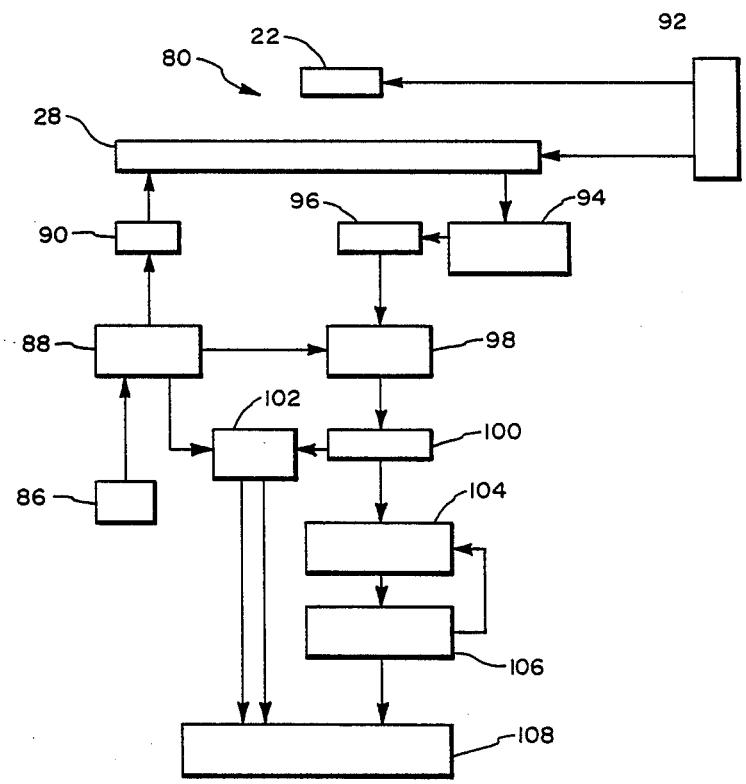
FIG. 5 is a schematic of the electronic components of the drop image sensor.

FIG. 5 schematically shows the electronic componentry of the present invention. In FIG. 5, it is seen that the componentry of the drop image sensor 10 of the present invention preferably includes a 10 mHz clock 86 which generates 10 million separate actions per second. Other clocks, of course, serve the same purpose. Clock 86 is operatively connected to a counter/timer 88 which separates the 10 million actions of clock 86 into cycles. Preferrably these cycles occur at the frequency of 2.5 kHz. As shown in FIG. 5, counter/timer 88 is connected to a receiver 90 which acts as an electronic interface between the counter/timer 88 and array 28. In accordance with the present invention, clock 86 and counter/timer 88 act electronically through receiver 90 to activate array 28 for operation of the liquid drop image sensor 10. To provide power for this operation a power source 92 is connected to both LED 22 and array 28. During activation of the liquid drop image sensor 10, as drops 18 pass through gap 80, a signal is generated by array 28 as previously discussed. This video signal which is generated by array 28 is electronically passed directly to a voltage comparator 94. As is well known by the skilled artesan, voltage comparator 94 comprises an analog to digital converter (ADC) which is incorporated in the present invention for digitizing the signal and presenting the signal from array 28 in discrete logic levels.

Voltage comparator 94 causes each discrete signal from array 28 to either be a one or a zero. Thus, marginal signals are cast either into the one or the zero category and a signal is generated by voltage comparator 94 which is a truly digital signal. A driver 96 interconnects voltage comparator 94 with digital filter 98 and supplies energy to move the signal between these two components. As will be appreciated by the skilled artesan, digital filter 98 is electronically connected with counter/timer 88 for the purpose of establishing predetermined time intervals during which meaningful signals are processed. In accordance with these connections, digital filter 98 selectively establishes the digital signal to be used for computation of the volume of a liquid drop 16. The selected digital signal is passed from digital filter 98 by electronic means to a squaring element 100 where the digital signal is squared and passed to an accumulator 104 for further computation.

Also shown connected to the squaring element 100 is a failsafe 102 which monitors the computations made by squaring element 100. Failsafe 102 provides a signal to alarm and stop operation of the liquid drop image sensor 10 when the signals monitored by failsafe 102 indicate either that the signal has no meaning or that a dangerous situation has developed. Signals which are within the proper range are allowed to pass directly from the squaring element 100 into the accumulator 104 and into register 106. The purpose of accumulator 104 and register 106 is to gather all signals associated with the same drop 18. This is done by collecting signals only during a particular time frame. As will be understood by those skilled in the pertinent art, the signals from failsafe 102 and from register 106 are passed directly into a microcontroller 108 where further computations are made and wherein overall control of the liquid drop image sensor 10 is provided. It is within the microcontroller 108 that the solution of the algorithm leading to a profile of the shadow 56 of drop 18 is accomplished. Microcontroller 108, also accomplishes the computations for determining the liquid volume of drop 18.

OPERATION

In its operation, liquid drop image sensor 10 of the present invention is associated with a drip chamber 12 and aligned therewith for establishing a path 26 for collimated light above fluid level 54. The light path 26 established between LED 22 and array 28 will be interrupted or broken by drops 18 as they fall through drip chamber 12. As a drop 18 leaves drop former 16 and passes through drip chamber 12, it triggers circuitry within the liquid drop image sensor 10 to activate LED 22 and array 28. When drop 18 interrupts light path 26, array 28 is operated in discrete sequential episodes to provide signals that are used by microcontroller 108 for purposes of calculating the volume of drop 18. Specifically, clock 86 and counter/timer 88 establishes episodic sequential operation of array 28. More specifically, the 10 mHz clock 86 provides 10 million functions per second which are broken into cycles by counter/timer 88.

In accordance with the present invention, each cycle comprises 400 separate actions and is subdivided into two time frames. One time frame is 110 microseconds in duration and the second is 290 microseconds in duration. As intended by the present invention, during the 290 microsecond period, the light sensors of pixels (not shown) on array 28 are activated and light from LED 22 which passes along path 26 is incident upon array 28. It is during this 290 microsecond period that a signal is generated by array 28 according to whether the pixel is within the shadow 56 of drop 18 or is in area 60 where direct light falls on the array 28. At the end of the 290 microsecond period, array 28 is registered. The time frames given here are only representations of the values used for the present invention. Other time frames can be easily used without departing from the intent of the present invention.

During registration of array 28, the video signal is passed to voltage comparator 94 where it is digitized. The result is a digital signal which has been cleaned up to comprise a series of digital signals which are equivalent either to a one or a zero, i.e. it is digitized and brought to a logic level. This operation is particularly important for those few sensors or pixels (not shown) which may have been exposed to energy from LED 22 that is somewhere between a complete shadow 56 and a direct light situation represented by area 60. Although the use of collimated light is intended to greatly reduce this problem, it can happen. Therefore, these in between signals are brought to a logic level which is equivalent to either being in the shadow 56 or the light area 60.

After being digitized by voltage/comparator 94 the digital signal is then passed by driver 96 to digital filter 98 where it is further refined in accordance with a temporal sequencing tht isolates meaningful information. More specifically, as regulated by counter/timer 88, digital filter 98 is able to distinguish signals from voltage comparator 94 which should be expected as deop 18 passes through gap 80 from those which should not be expected from this physical occurrence. This signal is then passed on through various componentry where it is used for the solution of an algorithm that leads to a determination of the liquid volume of the drop 18. The accumulator 104 and register 106 are useful in this process to isolate all signals which logically belong to the same liquid drop 18.

Depending upon the particular desires of the manufacturer-operator of the liquid drop image sensors of the present invention, two different means of calculating the volume of a drop can be used. In one calculation, ellipsoidal fit is accomplished. Under this method, since the spacing between individual elements of the CCD array 28 is accurately known, it is possible to calculate the value of the individual line scans of the drop 18 as it falls through the gap 80. With knowledge of the time interval between sequential scans of array 28 and the velocity of the falling drop which is dependent on the distance between light path 26 and the drop former 16, the Z coordinate of drop 18 can be determined. Using the width and height of the various scans and the Z coordinate of the drop, a least squares analysis is performed in microcontroller 108 to obtain values of the semi-major and semi-minor axes of the drop 18. These values are then used to obtain the volume of the liquid drop. This volume multiplied by the density of the particular fluid will give the mass of the drop 18. For purposes of calculation, a density of unity is established for water.

Another method of computing the volume of drop 18 is the "slice" method wherein the volume of drop 18 is computed by slicing drop 18 into discs and summing the contributions $V_i$ to determine the volume of the drop. In this method of calculation:

$$V_i = h\, D_i$$

where $D_i$ is the slice diameter and h is its thickness. As intended by the present invention, this computation can be made electronically by microcontroller 108.

While the particular liquid drop image sensor as herein shown and disclosed in detail is fully capable of obtaining the objects and providing the advantages hereinbefore stated, it is to be understood that it is merely illustrative of the presently preferred embodiments of the present invention and that no limitations are intended to the details of construction or design herein shown other than as described in the appended claims.

I claim:

1. An apparatus for measuring the volume of a drop of fluid comprises:
   means for providing a falling drop of fluid;
   a single light beam emitter;
   a single array of linearly aligned light sensors positioned from said light emitter to receive light energy therefrom and form a gap therebetween;
   means for sequentially activating said light emitter as said drop passes through said gap to cast a shadow of said drop on said array to generate a series of signals, each of said signals representing a separate cross-sectional width of said drop;
   a collimating lens positioned between said emitter and said array to direct collimated light across said gap; an aperture positioned between said emitter and said lens to limit the divergence of said light beam; and
   means to use said signals for calculating the fluid volume of said drop.

2. An apparatus as recited in claim 1 wherein said signal is determined by the proportion of linearly aligned light sensors affected by the shadow of said drop.

3. An apparatus as recited in claim 2 further comprising means to digitize said signal into logic levels.

4. An apparatus as recited in claim 3 wherein said means for providing a falling drop of fluid is a drop former positioned at a predetermined distance above said light emitter.

5. An apparatus as recited in claim 4 wherein light from said light emitter is infra-red light energy.

6. An apparatus for measuring the volume of a drop of fluid as recited in claim 1 further comprising means to activate said array to sequentially measure the width of said drop in ascertainable intervals at discreet cross sections with said signal proportional thereto.

7. A liquid drop image sensor for determining drop volume comprises:
   means for providing a falling drop of fluid;
   a single light beam source;
   a single array of linearly aligned light sensors spaced a predetermined distance from said light source to form a passageway therebetween;
   a collimating lens positioned between said light source and said array to direct collimated light across said passageway;
   an aperture positioned between said emitter and said lens to limit the divergence of said beam;
   means responsive to said drop to activate said array for discrete episodes while said drop is falling through said passageway to generate a series of signals, each of said signals representing a separate cross-sectional width of said drop; and
   means to accumulate said signals for calculating the volume of said drop.

8. A liquid drop image sensor as recited in claim 7 further comprising a collimating lens positioned between said light source and said array to direct collimated light across said passageway.

9. A liquid drop image sensor as recited in claim 8 further comprising electronic means to activate said light source and said array during passage of said drop through said passageway.

10. A liquid drop image sensor as recited in claim 9 further comprising means to digitize said signals.

11. A liquid drop image sensor as recited in claim 10 wherein light energy from said light source is infra-red light energy.

12. An image sensor for determining the volume of a liquid drop comprises:
   a single light beam emitter;
   a single array of linearly aligned light sensors positioned to establish a gap between said emitter and said array;

a collimating lens positioned between said light emitter and said array to direct collimated light across said gap;

an aperture positioned between said emitter and said lens to limit the divergence of said beam;

means to direct said drop through said gap;

means to sequentially activate said array for sensing light from said emitter during discrete episodes while said drop is falling through said gap;

counting means to establish a signal during each episode, each of said signals representing a separate cross-sectional width of said drop; and means to accumulate said signals from said counting means for calculating the volume of said drop.

13. An image sensor as recited in claim 12 further comprising trigger means to activate said light emitter and said array during the passage of said drop through said gap.

14. An image sensor as recited in claim 13 further comprising means to digitize said signal.

15. An image sensor as recited in claim 14 wherein said light energy from said light emitter is infra-red.

16. An image sensor as recited in claim 15 further comprising a drop former for directing drops through said gap, said drop former being positioned at a predetermined distance above said light emitter.

17. An image sensor as recited in claim 16 wherein said array comprises a series of light sensors linearly disposed with relationship to each other.

18. A liquid drop image sensor for determining drop volume comprises:

means for providing a falling drop of fluid;

a single light beam source;

a single array of linearly aligned light sensors spaced a predetermined distance from said light source to form a passageway therebetween;

a collimating lens positioned between said light source and said array to direct collimated light across said passageway;

an aperture positioned between said emitter and said lens to limit the divergence of said beam;

means responsive to said drop to sequentially activate said array while said drop is falling through said passageway to generate a series of signals, each of said signals representing a separate cross-sectional width of said drop; and means to evaluate said signals for calculating the volume of said drop.

19. A liquid drop image sensor as recited in claim 18 further comprising means to digitize said signal.

* * * * *